United States Patent [19]

Suzuki

[11] Patent Number: 5,616,029
[45] Date of Patent: Apr. 1, 1997

[54] DENTAL TREATMENT DEVICE FOR FORMING SCREW HOLE FOR EMBEDMENT OF IMPLANT MATERIAL

[75] Inventor: Tetsuji Suzuki, Utsunomiya, Japan

[73] Assignee: Nakanishi Dental Mfg. Co., Ltd., Tochigi-Ken, Japan

[21] Appl. No.: 494,473

[22] Filed: Jun. 26, 1995

[30] Foreign Application Priority Data

Jun. 27, 1994 [JP] Japan .................................. 6-144764

[51] Int. Cl.⁶ ...................................................... A61C 1/07
[52] U.S. Cl. ............................................. 433/122; 433/118
[58] Field of Search ................................. 433/105, 114, 433/117, 118, 122, 126, 127, 133

[56] References Cited

U.S. PATENT DOCUMENTS

| | | | |
|---|---|---|---|
| 4,222,738 | 9/1980 | Strohmaier | 433/105 |
| 4,245,985 | 1/1981 | Eibofner et al. | 433/105 |
| 4,718,851 | 1/1988 | Kuhn | 433/122 |

FOREIGN PATENT DOCUMENTS

| | | | |
|---|---|---|---|
| 525649 | 2/1993 | European Pat. Off. | 433/114 |
| 2118836 | 11/1983 | United Kingdom | 433/114 |

*Primary Examiner*—Ren Yan
*Attorney, Agent, or Firm*—Malcolm B. Wittenberg

[57] ABSTRACT

A dental treatment device for forming a screw hole for embedment of an implant material by a tool attached to the dental treatment device contains a speed-reducing unit for decelerating rotation of an external electric motor and raising torque for transmitting rotation to the tool, and a clutch unit provided between the speed-reducing unit and the tool. The clutch unit contains a driving side clutch having a first indented surface on its forward side, a tool side clutch having a second indented surface on its rear side, and a spring for thrusting the driving side clutch towards the tool side clutch for axially mating the first indented surface and the second indented surface with each other.

4 Claims, 4 Drawing Sheets

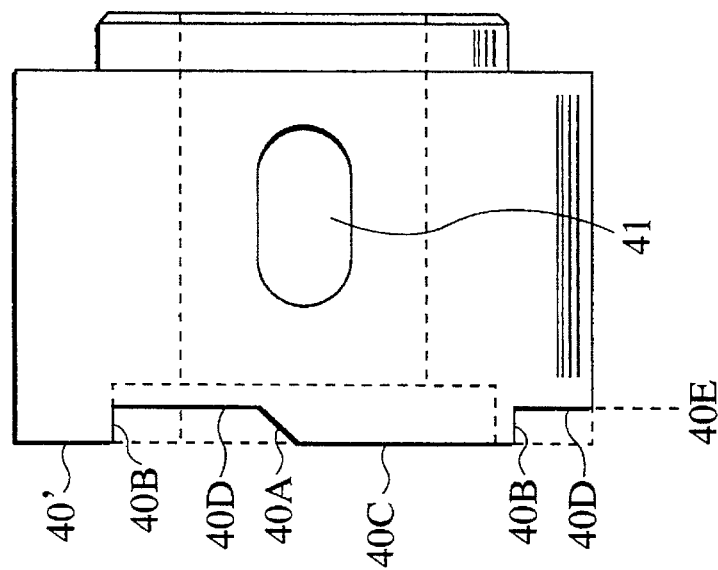
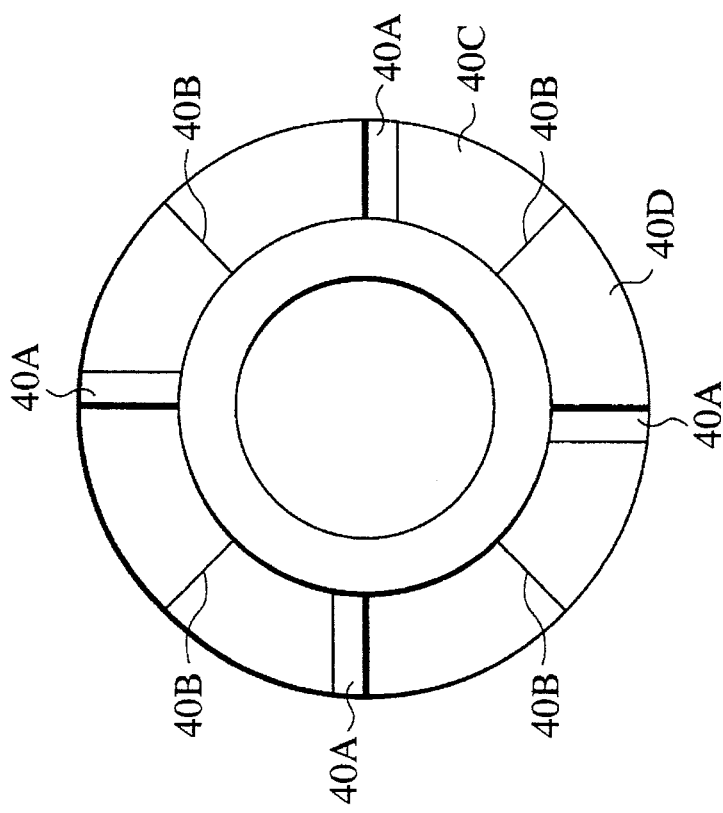

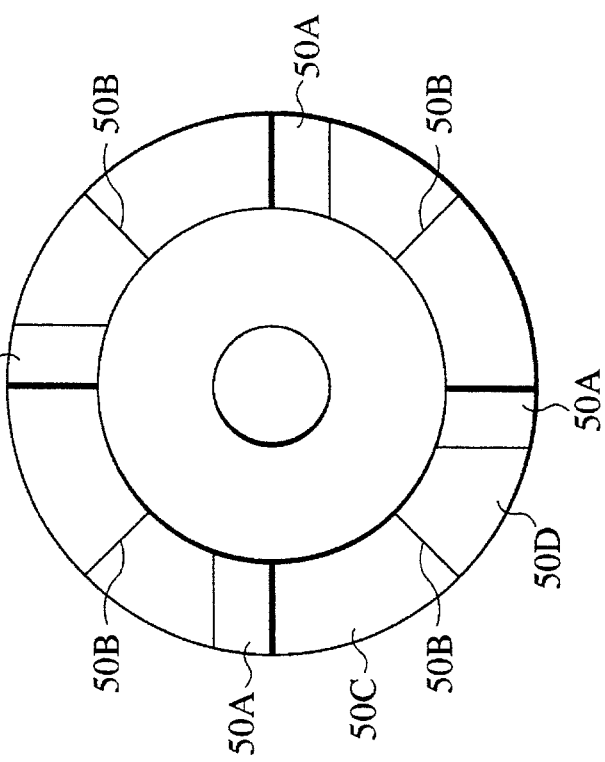
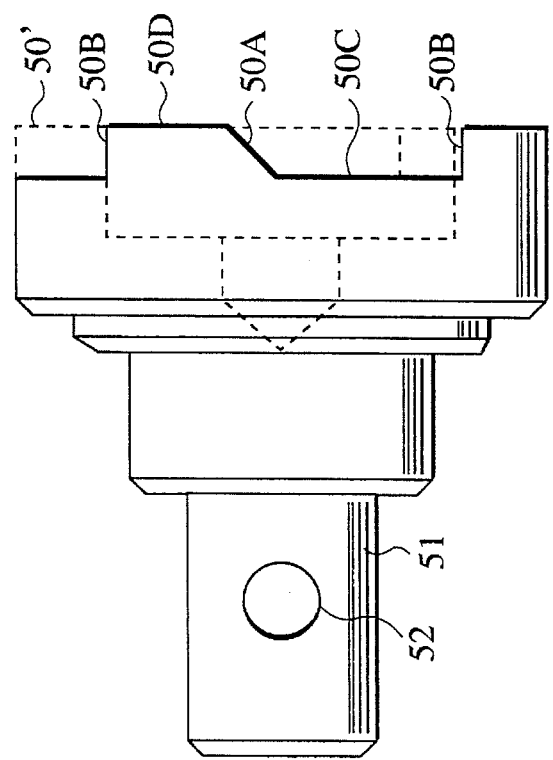

DENTAL TREATMENT DEVICE FOR FORMING SCREW HOLE FOR EMBEDMENT OF IMPLANT MATERIAL

BACKGROUND OF THE INVENTION

This invention relates to a dental treatment device and, more particularly, to a dental treatment device for forming a screw hole for embedment of an implant material.

The conventional practice for stable maintenance of a denture has been to bury an implant material in the jaw bone below the soft tissue of a missing tooth and to set the denture thereon. The implant material is previously molded to have a threaded surface via which the material is screwed into a screw hole in the treated site formed by a tool bur of a dental treatment device. On the other hand, if a countertorque during formation of the screw hole exceeds an allowable value, an excess load is applied to the tool bur, thus giving rise to collapsed screw crests or errors in screw depth to thereby produce hindrance in the mounting of the implant material and occasionally the fracture of the dental treatment device. In order to prevent these drawbacks, there is known a dental treatment device in which a clutch unit is provided between an external electric motor and a speed-reducing unit for decelerating the rotation of the motor for affording a high torque necessary to form the screw hole. The clutch unit includes a motor side clutch plate and a tool side clutch plate in which a pair of indented surfaces of the clutch plates are axially engaged with each other by a spring. The dental treatment device is so designed that, when the tool bur is over-loaded, the indented surfaces are disengaged from each other against the bias of the spring and the motor side clutch plate is rotated with a click movement relative to the tool side clutch plate for reducing the torque of the tool bur.

With the conventional dental treatment device, in which the clutch unit is provided between the motor and the speed-reducing unit, those members which are disposed between the tool bur and the speed-reducing unit or between the speed-reducing unit and the motor side clutch plate, and which are relatively fragile against overload, such as a gear or a pin member for securing the gear to a rotary shaft, tend to be fractured during the time the countertorque is transmitted from the tool bur to the clutch unit. On the other hand, since the countertorque reached at the speed-reducing unit is increased in inverse proportion to a reciprocal of the deceleration ratio of the speed-reducing unit, the spring force of the spring responsible for adjustment of the disengagement of the indented surfaces from each other is difficult to set to a proper value.

SUMMARY OF THE INVENTION

It is therefore an object of the present invention to provide a dental treatment device in which the spring force of the spring may be set to a proper value without the risk of the internal members being fractured under the countertorque.

The above and other objects of the invention will become apparent from the following description.

According to the present invention, there is provided a dental treatment device for forming a screw hole for embedment of an implant material by a tool attached to the dental treatment device comprising a speed-reducing unit for decelerating rotation of an external electric motor and raising torque for transmitting rotation to the tool, and a clutch unit provided between the speed-reducing unit and the tool, the clutch unit comprising a driving side clutch having a first indented surface on its forward side, a tool side clutch having a second indented surface on its rear side, and a spring for thrusting the driving side clutch towards the tool side clutch for axially mating the first indented surface and the second indented surface with each other, the first indented surface comprising a plurality of alternately and circumferentially formed indentations thereon, each indentation having a first inclined surface inclined relative to a cross-section extending perpendicularly to and diametrically of the clutch unit and a flat surface contiguous to the first inclined surface and terminating at a first vertical surface perpendicular to the cross-section, the second indented surface comprising a plurality of alternately and circumferentially formed indentations thereon, each indentation having a second inclined surface inclined relative to the cross-section and a flat surface contiguous to the second inclined surface and terminating at a second vertical surface perpendicular to the cross-section, rotation during forming of the screw hole by the tool being transmitted from the driving side clutch to the tool side clutch via the first and second indented surfaces, the first inclined surfaces of the first indented surface riding on the second inclined surfaces against bias of the spring when a countertorque exceeding an allowable limit value is applied to the tool for interrupting rotation from the driving side clutch to the tool side clutch.

BRIEF DESCRIPTION OF THE DRAWINGS

FIGS. 2a and 2b are a front view and a side view of a driving side clutch member, respectively.

FIGS. 3a and 3b are a side view and a rear view of a tool side clutch member, respectively.

PREFERRED EMBODIMENT OF THE INVENTION

The present invention will be explained in detail hereinbelow.

Figure 1:
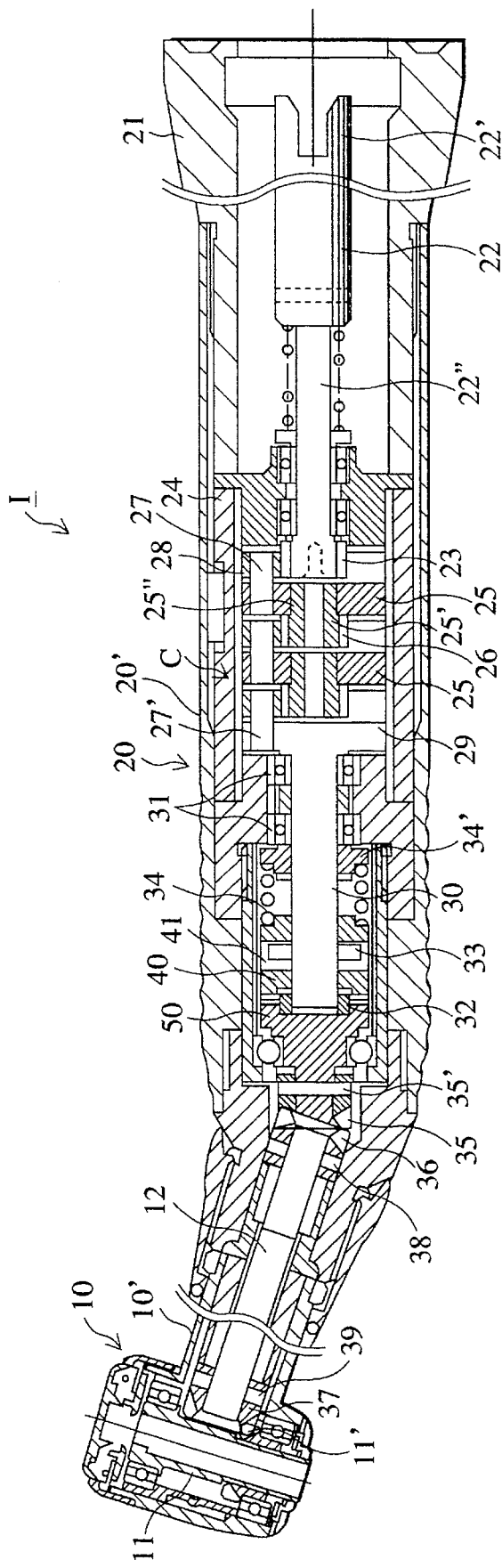
FIG. 1 is a cross-sectional view showing a dental treatment device according to the present invention.

FIG. 1 shows a dental treatment device I which is an angle-type handpiece having a head part 10 and a grip part 20, with the head part 10 being inclined with respect to the grip part 20. A tool bur, not shown, for forming a screw hole for burying an implant material therein is detachably mounted in a bur sleeve 11 within the head part 10 by a collet chuck. A transmission member 22 mounted within a proximal end casing 21 of the grip part 20, has a rear coupling 22' and a forward shaft portion 22". The coupling 22' is connected to an electric motor, not shown. The forward shaft portion 22" is carried by a bearing and has a gear 23 at its forward side. The gear 23 is engaged with rearmost planetary gears; 28 provided in a speed-reducing unit C mounted in the grip casing 20'.

The speed-reducing unit C has a tubular sun gear 24 having teeth on its inner peripheral surface, and two discs 25 mounted coaxially within the inside of the sun gear 24. The speed-reducing unit C also has two center shafts 25' extending forwardly from center holes 25" of the discs 25 and two transmission gears 26 mounted on the outer periphery of the center shafts 25'. The speed-reducing unit C further includes a plurality of supporting shafts 27 extending rearwardly from the vicinity of the outer periphery of each disc 25 and a plurality of planetary gears 28 mounted on the supporting shafts 27 and adapted for performing rotation about the center shafts 25' as the center of rotation.

Although not shown, three of the supporting shafts 27 are provided in each disc 25. These supporting shafts 27 are mounted at equiangular distances (120°) in the circumferential direction of the disc 25. The planetary gears 28 are mounted on each supporting shaft 27.

A driving shaft 30 is mounted ahead of the speed-reducing unit C and has a disc portion 29 which is increased in diameter at its rear end. The disc portion 29 is fitted with three supporting shafts 27' extending from the outer rim of the disc potion 29 towards rear. Each supporting shaft 27' supports the foremost planetary gears 28 of the speed-reducing unit C.

The speed-reducing unit C can be taken out from the grip part 20 so as to be exchanged with another unit having a different speed-reducing ratio.

The driving shaft 30 has its rear portion rotatably supported by bearings 31 and carries a pin member 33 near its forward portion. The pin member 33 is passed diametrically through the driving shaft 30 and protruded at both ends from the outer periphery of the shaft 30 into engagement with elongated openings 41 (FIG. 2b) formed in a driving side clutch member 40 adapted for accommodating the forward portion of the driving shaft 30.

FIGS. 2a and 2b show the driving side clutch member 40 having at its front end a first indented surface 40', a rear portion of which is substantially cylindrically shaped for accommodating the foremost portion of the driving shaft 30. Two elongated openings 41 are formed in diametrically opposite portions in the outer peripheral surface of the driving side clutch member 40 for accommodating both ends of the pin member 33.

The first indented surface 40' has plural first inclined surfaces 40A inclined with respect to cross-section 40E extending perpendicularly to and diametically of the driving side clutch member 40, and plural first vertical surfaces 40B perpendicular to the cross-section 40E. The first inclined surfaces 40A and the first vertical surfaces 40B alternate each other at pre-set intervals along the circumferential direction of the driving side clutch member 40 for delimiting protrusions 40C and recesses 40D in the first indented surface 40'.

The driving side clutch member 40 is resiliently thrust from its rear end by a coil spring 34 towards a tool side clutch member 50 provided ahead of the driving side clutch member 40.

FIGS. 3a and 3b show the tool side clutch member 50 having at its rear end a second indented surface 50' engageable with the first indented surface 40' of the driving side clutch member 40.

Figure 4:
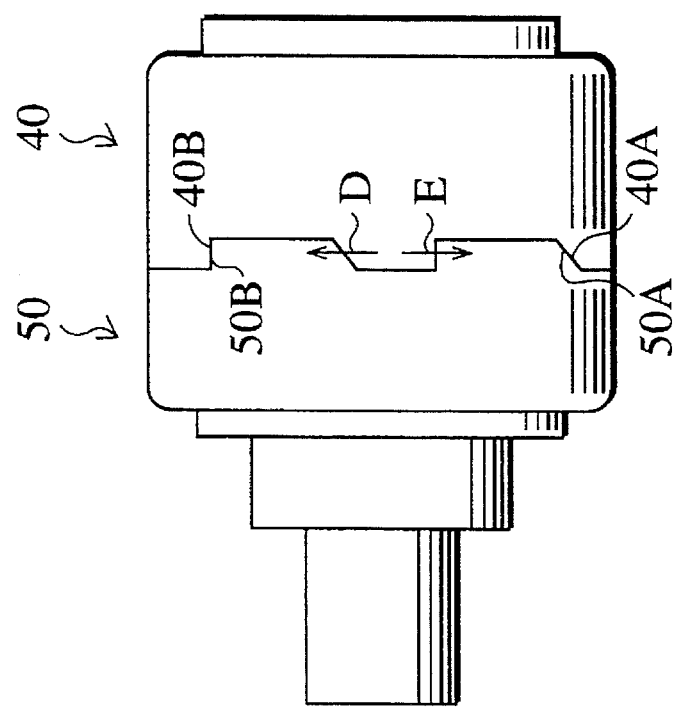
FIG. 4 is a side view showing the driving side clutch member engaged with the tool side clutch member.

Similarly to the first indented surface 40', the second indented surface 50' has plural second inclined surfaces 50A and plural second vertical surfaces 50B. The second inclined surfaces 50A and the second vertical surfaces 50B alternate each other along the circumferential direction of the tool side clutch member 50 for delimiting protrusions 50D and recesses 50C which are complementary to those of the first indented surface 40'. Thus the first indented surface 40' and the second indented surface 50' are hated with each other under the thrusting force of the coil spring 34, as shown in FIG. 4. The coil spring 34 has its rear end supported by a spring retainer 34' secured at a mid portion of the outer peripheral surface of the driving shaft 30. The tool side clutch member 50 has a forward protruding portion 51 of reduced diameter and a through-hole 52 passing through the protruding portion 51 in the diametral direction. A gear 35 is mounted on the protruding portion 51 via a pin member 35' passed through the through-hole 52 (FIG. 1).

Turning again to FIG. 1, an anti-wobbling member 32 for stopping the wobbling of the driving shaft 30 is interposed between the outer peripheral surface of the foremost end of the driving shaft 30 and the inner sides of the first and second indented surfaces 40' and 50' by which the driving side clutch member 40 and the tool side clutch member 50 are engaged with each other.

The dental treatment device I has a rotary shaft 12 within an inclined portion 10' interconnecting the head part 10 and the grip part 20. The foremost and rear ends of the rotary shaft 12 carry gears 37, 36 via pin members 39, 38, respectively. The rear end gear 36 meshes with the gear 35 provided at the foremost end of the tool side clutch member 50, while the forward side gear 37 meshes with a gear 11' formed on the outer peripheral surface of the bur sleeve 11 within the head part 10.

Rotation of the external electric motor is transmitted via the gear 23 of the transmission member 22 to the speed-reducing unit C. The speed-reducing unit C decelerates the rotation by the operation of a known sun-and-planet gears and raises the torque. Rotation is then transmitted from the driving shaft 30 via the pin member 33 to the driving side clutch member 40. The driving side clutch member 40 runs the tool side clutch member 50 in rotation in a direction indicated by arrow D in FIG. 4. At this time, rotation of the driving side clutch member 40 is transmitted substantially via the first and second inclined surfaces 40A, 50A to the tool side clutch member 50. Rotation of the tool side clutch member 50 is transmitted to the tool bur via the pin member 35', the gears 35, 36, the pin member 38, the rotary shaft 12, the pin member 39, the gears 37, 11' and the bur sleeve 11.

If, while a screw hole for embedment of the implant material is tapped by the tool bur, a countertorque exceeding an allowable range is applied to the tool bur, the countertorque is transmitted from the tool bur to the tool side clutch member 50 through a route which is reversed from the above-mentioned route to reduce the rotational velocity of the tool side clutch member 50. Thus the first inclined surfaces 40A of the driving side clutch member 40 tending to maintain the rotational velocity of the tool side clutch member 50 ride on the second inclined surfaces 50A of the tool side clutch member 50 against the bias of the coil spring 34 to disengage the first and second indented surfaces 40', 50' from each other. This causes the driving side clutch member 40 to be rotated in idle or by click movement to reduce the torque transmitted from the tool side clutch member 50 to the tool bur to eliminate the load applied to the tool bur. Thus it becomes possible to avoid a situation in which the screw hole is bored too deeply or the thread crest becomes collapsed.

On the other hand, since the clutch mechanism composed of the driving side clutch member 40 and the tool side clutch member 50, is mounted forwardly of the speed-reducing unit C and thus is disposed closer to the tool bur, the countertorque is transmitted from the tool bur to the tool side clutch member 50 promptly, without being transmitted further rearwards beyond the speed-reducing unit C. Thus the countertorque is not increased in proportion to the reciprocal of the deceleration ratio of the speed-reducing unit C. The component parts more vulnerable to over-loads, such as the gears 11', 35, 36, 37 and the pin members 35', 38, 39, are not damaged by the countertorque because the overload state is quickly annulled by the clutch mechanism. On the other hand, the force of the coil spring 34 for reliably disengaging the first and second indented surfaces 40', 50' from each other in case of necessity and the torque setting as over-load inhibiting means may be easily set to desired proper value.

After tapping the screw hole to a required depth, the electric motor is rotated in reverse so that the tool bur is also rotated in reverse so as to be pulled out of the screw hole. At this time, rotation from the driving side clutch member 40 to the tool side clutch member 50 is transmitted via the first vertical surfaces 40B and the second vertical surfaces 50B, as shown by arrow E in FIG. 4. Consequently, there is no risk of the driving side clutch member 40 and the tool side clutch member 50 being disengaged from each other due to the first and second inclined surfaces 40A, 50A of the driving side clutch member 40 and the tool side clutch member 50 riding one on the other in the tool bur take out step from the screw hole for which there is no necessity of taking the countertorque into account. This enables smooth and reliable removal of the tool bur from the screw hole.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental treatment device for forming a screw hole for embedment of an implant material by a tool attached to said dental treatment device comprising a speed-reducing unit for decelerating rotation of an external electric motor and raising torque for transmitting rotation to the tool, and a clutch unit provided between the speed-reducing unit and the tool, said clutch unit comprising a driving side clutch having a first indented surface on its forward side, a tool side clutch having a second indented surface on its rear side, and a spring for thrusting said driving side clutch towards the tool side clutch for axially mating the first indented surface and the second indented surface with each other, said first indented surface comprising a plurality of alternately and circumferentially formed indentations thereon, each indentation having a first inclined surface inclined relative to a cross-section extending perpendicularly to and diametrically of the clutch unit and a flat surface contiguous to said first inclined surface and terminating at a first vertical surface perpendicular to said cross-section, said second indented surface comprising a plurality of alternately and circumferentially formed indentations thereon, each indentation having a second inclined surface inclined relative to said cross-section and a flat surface contiguous to said second inclined surface and terminating at a second vertical surface perpendicular to said cross-section, rotation during forming of said screw hole by said tool being transmitted from the driving side clutch to the tool side clutch via said first and second indented surfaces, the first inclined surfaces of said first indented surface riding on the second inclined surfaces against bias of the spring when a countertorque exceeding an allowable limit value is applied to said tool for interrupting rotation from said driving side clutch to said tool side clutch.

2. The dental treatment device as claimed in claim 1 wherein, during extraction of said tool from the screw hole, the driving side clutch is rotated in reverse for rotating the tool side clutch via said first and second vertical surfaces for preventing the driving side clutch from being disengaged from the tool side clutch.

3. The dental treatment device as claimed in claim 1 wherein said speed-reducing unit includes a sun gear and a plurality of planetary gears.

4. The dental treatment device as claimed in claim 1 further comprising a driving shaft for interconnecting said driving side clutch and said speed-reducing unit and an anti-wobbling member for inhibiting wobbling of said driving shaft.

* * * * *